(12) United States Patent
Pacheco et al.

(10) Patent No.: US 8,044,247 B2
(45) Date of Patent: *Oct. 25, 2011

(54) PROCESS FOR THE PREPARATION OF FLUOROMETHYL 2,2,2-TRIFLUORO-1-(TRIFLUOROMETHYL) ETHYL ETHER

(75) Inventors: Ogari Pacheco, Itapira (BR); Antonio Carlos Teixeira, Itapira (BR); Edson Luiz Lima, Itapira (BR); Maria Alice Böckelmann, Itapira (BR)

(73) Assignee: Cristália Produtos Químicos Farmacêuticos Ltda., Itapira (BR)

( * ) Notice: Subject to any disclaimer, the term of this patent is extended or adjusted under 35 U.S.C. 154(b) by 185 days.

This patent is subject to a terminal disclaimer.

(21) Appl. No.: 12/443,440

(22) PCT Filed: Sep. 29, 2006

(86) PCT No.: PCT/BR2006/000198
§ 371 (c)(1),
(2), (4) Date: Mar. 27, 2009

(87) PCT Pub. No.: WO2008/037040
PCT Pub. Date: Apr. 3, 2008

(65) Prior Publication Data
US 2009/0247791 A1    Oct. 1, 2009

(51) Int. Cl.
*C07C 41/06*    (2006.01)

(52) U.S. Cl. ........ 568/682; 568/683
(58) Field of Classification Search .......... None
See application file for complete search history.

(56) References Cited

U.S. PATENT DOCUMENTS 6,100,434 A * 8/2000 Bieniarz et al. ............... 568/683

* cited by examiner

*Primary Examiner* — Rosalynd Keys
(74) *Attorney, Agent, or Firm* — Birch, Stewart, Kolasch & Birch, LLP

(57) ABSTRACT

The present invention refers to a process for the preparation of fluoromethyl 2,2,2-trifluoro-1-(trifluoromethyl)ethyl ether (sevoflurane) which includes a step that consists of reacting hexafluoroisopropanol with a formaldehyde equivalent selected among paraformaldehyde or 1,3,5-trioxane, a chlorinating agent selected from the group consisting of oxalyl chloride, phosphorus trichloride, phosphorus pentachloride, phosphorus oxychloride, sulfuryl chloride and thionyl chloride, and a strong acid selected from the group consisting of concentrated or fuming sulfuric acid resulting in the formation of the intermediate sevochlorane which is converted to sevoflurane in a second step which consists of reacting sevochlorane with an alkali metal fluoride, or a linear or branched chain tetra-alkyl quarternary ammonium fluoride in the presence of a sub-stoichiometric quantity of an alkali metal iodide, or a linear or branched alkyl chain tetra-alkyl quarternary ammonium iodide, preferably in a solvent.

18 Claims, 1 Drawing Sheet

PROCESS FOR THE PREPARATION OF FLUOROMETHYL 2,2,2-TRIFLUORO-1-(TRIFLUOROMETHYL) ETHYL ETHER

This Application is the National Phase Under 35 U.S.C. §371 of PCT International Application No. PCT/BR2006/000198 which has an International filing date of Sep. 29, 2009. The entire contents of all applications listed above are hereby incorporated by reference.

FIELD OF THE INVENTION

The present invention refers to the field of inhalation anesthetics. In particular, the present invention refers to a process for the preparation of sevoflurane and of an intermediate for the preparation of sevoflurane.

BACKGROUND OF THE INVENTION

Sevoflurane, whose chemical name is fluoromethyl 2,2,2-(trifluoro-1-trifluoromethyl)ethyl ether, was developed for use as an inhalation anesthetic.

The first reference, which describes the preparation of sevoflurane, is British patent GB 1,250,928, which describes the synthesis of 1,3-polyhalo-2-propyl ethers and the use of the same as anesthetics. The process employed consists of preparing the intermediate Sevochlorane, by free radical chlorination of 1,1,1,3,3,3-hexafluoro-2-propyl methyl ether with gaseous chlorine and luminous irradiation. This free radical chlorination results in a very low yield, being the practical yield in obtaining sevoflurane at the end of the process approximately 30% of the theoretical value. Sevoflurane is obtained by the reaction of sevochlorane with potassium fluoride in tetrahydrothiophene dioxide, commercially known as sulfolane, employing heating.

The vast majority of the commercial processes preferred for the preparation of sevoflurane rely on the use of hexafluoroisopropanol (HFIP) as starting material.

There are processes described in the literature in which sevoflurane is obtained directly from hexafluoroisopropanol without involving intermediates. This is the case, for example, of the processes for the synthesis of sevoflurane described in U.S. Pat. Nos. 4,250,334 and 4,469,898.

U.S. Pat. No. 4,250,334 describes a method for the synthesis of sevoflurane, consisting of the reaction of hexafluoroisopropanol with a mixture of hydrofluoric acid, paraformaldehyde and a dehydrating agent. Although it is a "one pot" method, during the production of sevoflurane and its subsequent distillation, a large quantity of hexafluoroisopropanol is co-distilled with the product, which results in large losses of this reagent, which is also an impurity, whose removal in posterior purification steps is critical, and difficult to accomplish. In addition to this inconvenience, the formation of side products is elevated, being that the final product is obtained, in an appropriate degree of purity, only after various purifications steps by fractional distillation.

U.S. Pat. No. 4,469,898 describes the synthesis of sevoflurane from hexafluoroisopropanol, hydrofluoric acid and a desiccating agent, in special equipment where unconsumed hexafluoroisopropanol is recycled. Various desiccating agents are employed such as sulfuric, phosphoric, trifluoromethanesulfonic acids, etc. The reported yields for this process are low and the isolated product presents low purity.

Particularly useful for the preparation of sevoflurane are those processes, which first prepare the intermediate sevochlorane, followed by fluorination through a halogen exchange reaction.

U.S. Pat. No. 6,100,434 describes the synthesis of sevoflurane through the preparation of sevochlorane and subsequent fluorination of this intermediate with potassium fluoride in a high molecular weight solvent. Sevochlorane is prepared from hexafluoroisopropanol, aluminum trichloride and 1,3,5-trioxane. An excess of aluminum trichloride in the reaction medium results predominantly in the formation of 2,2'-[methylenebis(oxy)]bis-(1,1,1,3,3,3-hexafluoropropane)—hereinafter denominated P1. The reaction is interrupted by addition of a 6N HCl solution to decompose the gel of hydroxydichloroaluminate. The authors relate that the isolated product contained 95% sevochlorane, <5% of P1 and <1% of polyacetals of higher molecular weight. The crude yield described was 87%. Among the disadvantages of this process is the fact that large quantities of aluminum trichloride must be handled, which is a highly hygroscopic solid and whose reaction with atmospheric humidity or with residual water present tends to be violent. The fact that this reagent easily reacts with water, resulting in the formation of acidic gasses, causes a reduction in its content, compromising considerably the yield of the reaction and the purity of the isolated product. The addition of a 6N hydrochloric acid solution to interrupt the reaction is an additional disadvantage of the process, violently elevating the reaction temperature, resulting in partial product loss by decomposition, volatilization and polymerization. Finally, this reaction generates as a residue, an aqueous phase containing hydroxyaluminates that require incineration for disposal, incurring additional costs.

U.S. Pat. No. 6,245,949 describes the synthesis of sevoflurane by the reaction of hexafluoroisopropanol with dimethoxymethane and the resulting product is submitted to reaction with aluminum trichloride and potassium fluoride. Once again there is the disadvantage of working with aluminum trichloride, which is hygroscopic and easily inactivated in the presence of humidity. The yield of the process is quite low, being declared by the author as 50%.

U.S. Pat. No. 6,271,422 describes the synthesis of sevoflurane by fluoromethylation of alcohols via decarboxylative halogenation. In this way, hexafluoroisopropanol is submitted to reaction with ethyl alpha-bromoacetate providing alpha-(hexafluoroisopropoxy) acetic acid in a yield of 66%. This intermediate is subjected to reaction with the highly toxic lead tetra-acetate, using the carcinogenic benzene as the solvent. In the reaction sequence, the homogeneous benzene/sevochlorane solution, which is inseparable by distillation, is reacted with potassium fluoride providing at the end of the process sevoflurane with a low yield of 28%.

U.S. Pat. No. 5,886,239 describes the synthesis of sevoflurane by reacting sevochlorane with the salt obtained from the reaction between sterically hindered tertiary amines, such as di-isopropylethylamine, and hydrofluoric acid. The process described is incomplete and results in low purity sevoflurane, which requires various purifications steps by fractional distillation to obtain a level of purity necessary for clinical use, which reduces considerably the yield declared by the inventors.

Various other references exist which describe the synthesis of sevoflurane employing uncommon reagents, or by way of processes, which are not industrially applicable due to their complexity or low yields.

The processes, which involve the reaction of hexafluoroisopropanol with the formation of the intermediate sevochlorane, are of particular interest. However, up to the present moment, there is no description of an efficient process for both steps, which can be easily adapted to commercial production of sevoflurane of high purity and yield.

Employing the processes described up to the present moment, the production of sevochlorane is problematic due to incomplete reactions with very low yields, or it requires difficult to handle or highly toxic reagents, or results in a product containing impurities difficult to separate.

For the conversion of sevochlorane to sevoflurane, in general, potassium fluoride (KF) is employed in a halogen exchange reaction. This reaction may result in low yields of sevoflurane due to parallel reactions, which result in elimination, hydrolysis and polymerization by-products.

Many of the processes which involve the synthesis of sevoflurane by reaction of sevochlorane with potassium fluoride (KF) employ between 2.5 and 7.0 equivalents of potassium fluoride (KF) per equivalent of sevochlorane and heating of the reaction medium for more than three hours. This excess of potassium fluoride (KF) is responsible for the formation of fluoromethyl 2,2-difluoro-1-(trifluoromethyl) vinyl ether (compound A), which has been shown to be nephrotoxic in rats and whose presence should be controlled in the final product. Heating for prolonged times leads to decomposition of the sevochlorane present in the reaction medium generating HFIP and fluorinated acetals reducing the yield and difficulting the isolation of a product with above 99.97% purity.

The conversion of sevochlorane to sevoflurane may employ between 1 and 2 equivalents of KF per molar equivalent of sevochlorane when the reaction is conducted in the presence of water as solvent and a phase transfer catalyst as described in patent WO2006/055748, however, a larger concentration of KF is important to obtain a better yield and to minimize the formation of hydrolysis products of sevochlorane. The object of this patent application, is a process for the conversion of sevochlorane to sevoflurane in water, whereby less than 5% of the starting sevochlorane is hydrolyzed.

As such, there exists the necessity of a process for the preparation of sevoflurane from hexafluoroisopropanol with the formation of the intermediate sevochlorane with high purity and high yield, and efficient conversion of sevochlorane to sevoflurane by halogen exchange reaction in such a way that the resulting product is obtained in high yield and purity.

SUMMARY OF THE INVENTION

The present invention describes a novel process for the preparation of sevoflurane, which results in good yields, and a product of a high degree of purity, and presents in the first step the additional advantage of being robust in the presence of atmospheric humidity, without compromising the reaction yield. In addition to these considerations, the process described in the present invention employs easily handled and transported reagents, and the residues generated may be easily treated.

According to one embodiment of the present invention, the process for the preparation of fluoromethyl 2,2,2-trifluoro-1-(trifluoromethyl)ethyl ether (sevoflurane) consists of the following steps:

chloromethylation reaction of hexafluoroisopropanol (HFIP) with: a formaldehyde equivalent, such as, but not limited to, paraformaldehyde (polymerized formaldehyde $(CH_2O)_n$) or 1,3,5-trioxane (the cyclic trimer of formaldehyde); a chlorinating agent such as, but not limited to, oxalyl chloride, phosphorus trichloride, phosphorus pentachloride, phosphorus oxychloride, sulfuryl chloride or, preferably, thionyl chloride; and a strong acid such as, but not limited to, concentrated or fuming sulfuric acid, while maintaining the reaction mixture under stirring to form the intermediate sevochlorane;

reacting sevochlorane with an alkali or alkaline earth metal fluoride, preferably potassium fluoride, or a linear or branched chain, tetra-alkyl quarternary ammonium fluoride, preferably tetrabutyl ammonium fluoride (TBAF), in the presence of a sub-stoichiometric quantity of an alkali or alkaline earth metal iodide, preferably KI, NaI and CsI, more preferably KI, or a linear or branched chain, tetra-alkyl quarternary ammonium iodide, preferably tetrabutyl ammonium iodide (TBAI), to form sevoflurane.

DESCRIPTION OF THE INVENTION

Figure 1:
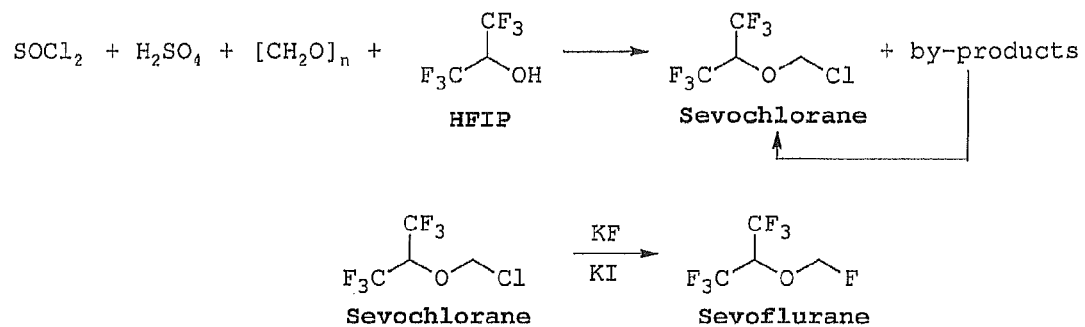
FIG. 1 is a schematic representation of a process for the preparation of sevoflurane according to the present invention.

According to the first step of the process of the present invention, chloromethyl 2,2,2-trifluoro-1-(trifluoromethyl) ethyl ether (sevochlorane) is prepared by chloromethylation reaction of hexafluoroisopropanol (HFIP) with: a formaldehyde equivalent such as, but not limited to, paraformaldehyde (polymerized formaldehyde $(CH_2O)_n$) or 1,3,5-trioxane (the cyclic trimer of formaldehyde); a chlorinating agent such as, but not limited to, oxalyl chloride, phosphorus trichloride, phosphorus pentachloride, phosphorus oxychloride, sulfuryl chloride or, preferably, thionyl chloride; and a strong acid such as, but not limited to, concentrated or fuming sulfuric acid.

The reaction temperature will vary according to the combination of reagents employed. Independently from what reagents are combined, the addition of the reagents may be conducted at temperatures ranging between −35° C. and 20° C., preferably below 20° C. After this addition step, the reaction temperature is kept between 0° C. and 60° C., preferably between 15° C. and 35° C.

The reaction is accomplished in an equipment consisting of a flask or reactor equipped with magnetic or mechanical stirring, thermometer, an addition funnel and a cooled condenser connected through a glass tube to a vessel containing a 30% sodium hydroxide solution to neutralize the HCl and $SO_2$ gasses released by the reaction.

The order of addition of the reagents HFIP, formaldehyde equivalent, a chlorination agent such as thionyl chloride and a strong acid such as sulfuric acid, is not critical, demonstrating the flexibility of the present process. Preferably, the procedure consists of introducing the reagents HFIP, the formaldehyde equivalent and thionyl chloride to the reaction flask. Sulfuric acid is slowly added under stirring, maintaining the reaction temperature below 20° C. The procedure may, alternatively, consist of introduction of the reagents HFIP, the formaldehyde equivalent and sulfuric acid to the reaction flask maintaining the internal temperature below 20° C. thereafter; thionyl chloride is slowly added. Also, alternatively, the hexafluoroisopropanol may be slowly added to the reaction mixture. The reaction is kept at a temperature ranging between 15° C. and 35° C., and is characterized by the release of gasses (HCl e $SO_2$) but, after a period of stirring, a separation of phases is observed.

Experiments have shown that the purity of the isolated product depends on the number of equivalents of thionyl chloride and formaldehyde employed, these reagents being preferably employed in excess in relation to HFIP. It was also observed that the use of formaldehyde in excess in relation to HFIP favors the separation of phases during the reaction, where the lower phase consists of an extremely acidic mixture, and the upper phase consists of the desired product, sevochlorane.

In a preferable embodiment of the present invention, the reaction, in the first step of the process, employs 1 equivalent of HFIP, 1.5 equivalents of paraformaldehyde (calculated considering the molecular weight of formaldehyde, $CH_2O$, equal to 30), 1.8 equivalents of thionyl chloride and 1.5 equivalents of sulfuric acid in order to produce sevochlorane with above 95% purity. Preferably, the addition of the reagents is conducted at temperatures between 0° C. and 20° C. The temperature varies at the beginning of the addition of sulfuric acid to the reaction mixture, and, due to this fact, the temperature in this step should be controlled to avoid HFIP losses and subsequent reduction in yield.

The reaction is monitored by gas chromatography (GC), where, initially, a mixture of products is formed which consists of sevochlorane and by-products. Surprisingly, the secondary by-products formed in the first few hours of the reaction, are converted to sevochlorane as the reaction progress, which, in this manner, does not affect the global yield of the desired product. This fact is contrary to the previously described processes, which also use HFIP as a raw material, wherein the formation of said by-products results in an effective reduction in chemical yield.

The by-products obtained in the present process are compounds already known and described in the preparation of sevochlorane and/or sevoflurane via other routes. The principal by-products identified in the first hours of the reaction, according to the present invention for the preparation of sevochlorane are:

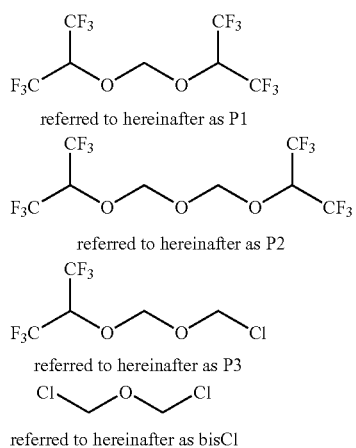

referred to hereinafter as P1 referred to hereinafter as P2 referred to hereinafter as P3 referred to hereinafter as bisCl

Interestingly, the initial formation of the by-products can be explained due to the initial reaction among paraformaldehyde, sulfuric acid and HFIP. The break of paraformaldehyde during the addition of sulfuric acid to the reaction medium explains the observed exothermic process that is controlled by keeping the temperature below 20° C. During the elapsing of the reaction chlorosulfonic acid is slowly formed in the reaction medium, through an endothermic reaction of sulfuric acid with thionyl chloride. The chlorosulfonic acid, generated in situ, reacts with the by-products mixture, through an exothermic reaction, with formation of the sevochlorane. In that way a thermal compensation is observed during the elapsing of the reaction allowing the same to happen in a soft way, and the product is obtained with high yield and purity, without direct contact with the corrosive chlorosulfonic acid.

Sevochlorane produced according to the first step of the process of the present invention may be isolated from the reaction medium by separation of the liquid phases of the reaction medium, or if this separation does not occur naturally, water can be added to the reaction medium keeping the temperature between 0° C. and 10° C., followed by separation of the phases.

The crude sevochlorane isolated is treated first with an aqueous alkaline solution to correct the pH followed by a second aqueous alkaline solution to remove by-products formed in the reaction. The sevochlorane has a very low solubility in water being present in the lower phase while water-soluble impurities will be present in the upper aqueous phase. The sevochlorane may be separated from the aqueous phase by conventional techniques.

According to the present invention, the crude sevochlorane is treated first with an alkaline solution to remove the excess of acids and to adjust the pH. The alkaline solution employed may be an aqueous solution of an alkali or alkaline earth metal carbonate or hydroxide, or ammonia. Preferably the sevochlorane is treated with a 10% sodium carbonate solution in sufficient quantity to result in a neutral pH.

The product, sevochlorane, at neutral pH is then treated with a second alkali or alkaline earth metal hydroxide solution, preferably a 10% sodium hydroxide solution, to facilitate the decomposition and removal of residual by-products like bis-chloromethyl ether—bisCl. The sevochlorane may be separated from the aqueous phase by conventional techniques.

The sevochlorane obtained according to the present invention may be converted to sevoflurane in the reaction medium containing potassium fluoride (KF) and purified by fractional distillation according to procedures described in the art, however, this conversion is advantageously conducted according to the second step of the process in the present invention.

According to this step, sevochlorane is converted to fluoromethyl 2,2,2-trifluoro-1-(trifluoromethyl)ethyl ether (sevoflurane) using an alkali or alkaline earth metal fluoride, preferably KF, or a linear or branched chain tetra-alkyl ammonium fluoride, and a sub-stoichiometric quantity of an alkali or alkaline earth metal iodide, preferably KI, NaI and CsI, and more preferably KI, or a linear or branched chain tetra-alkyl ammonium iodide, such as tetrabutyl ammonium iodide (TBAI).

Figure 2:
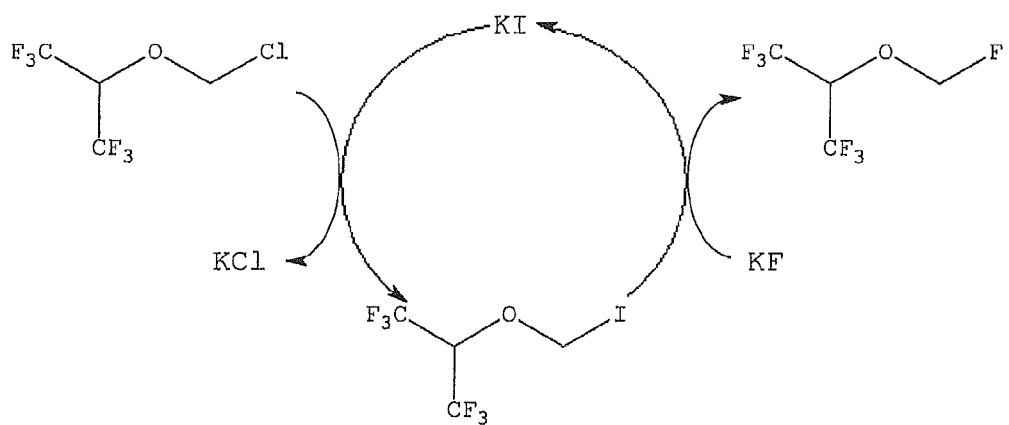
FIG. 2 represents the second step of the process of the present invention.

FIG. 2 represents the second step of the process of the present invention showing the formation of iodomethyl 2,2,2-trifluoro-1-(trifluoromethyl)ethyl ether, a more reactive intermediate than sevochlorane, which is then converted to sevoflurane.

The reaction of sevochlorane with an alkali metal halide (for example: KF, KI) results in halogen exchange via a nucleophilic substitution reaction known as the Finkelstein reaction. The halogen exchange depends upon the nucleophilicity of the anion among others factors. Among the halogens, iodide is the best leaving group, followed by bromide, chloride and fluoride.

In the second step of the process of the present invention, the use of a sub-stoichiometric quantity of KI in addition to KF results in an increase in the velocity of the reaction of the conversion of sevochlorane to sevoflurane.

The increase in the velocity of the conversion of sevochlorane to sevoflurane implies in a reduction of the exposition time of the product to heating, diminishing the quantity of decomposition products. As the reaction is preferably conducted in the presence of a solvent, the reaction conditions should be optimized for each solvent in order to obtain the best yield and purity of the product.

The halogen exchange reaction is accomplished in a flask or reactor equipped with magnetic or mechanical stirring, thermometer and a refrigerated condenser.

The reaction in the second step of the process may be conducted in different manners. The order of addition of the reagents is not critical. The procedure consists of introducing the reagents sevochlorane, potassium fluoride (KF) and potassium iodide (KI) in the reactor maintaining the reaction mixture under stirring and reflux, for a period of time or until the complete conversion of sevochlorane to sevoflurane. Alternatively, the procedure consists of the introduction of the reagents sevochlorane, potassium fluoride and potassium iodide in the reactor, maintaining the reaction mixture under reflux and removing the sevoflurane formed by selective fractional distillation. Yet, in another manner, the procedure may consist of the introduction of the reagents sevochlorane, potassium fluoride and potassium iodide to the reactor, which is closed generating a pressure in the range of 0 to 30 p.s.i., and maintaining the reaction mixture under stirring and heating. After the complete conversion of the sevochlorane to sevoflurane, the product is cooled and isolated by the addition of water. The crude sevoflurane is separated and purified by fractional distillation.

The reaction in the second step of the process is preferably conducted at a temperature between 60° C. and 100° C., however, the temperature will depend on the chosen solvent.

The reaction time may vary between 1 and 6 hours depending on the temperature at which the reaction mixture is maintained, in other words, at higher temperatures, the reaction is faster. The reaction time also depends on the way the reaction is conducted and on the chosen solvent.

The alkali or alkaline earth metal fluorides, or the linear or branched chain tetra-alkyl quarternary ammonium fluoride, which may be used as the fluorinating agent in the second step of the process of the present invention, include, but are not limited to, NaF, KF, $KF_2H$, $NaF_2H$, CsF, $CaF_2$, $MgF_2$, $SrF_2$ or tetrabutyl ammonium fluoride (TBAF). Preferably, potassium fluoride (KF) is employed in the reaction. Potassium fluoride (KF) may be in the form of its dihydrate or its tetrahydrate. The reaction employs between 1 and 3 equivalents of potassium fluoride (KF) for each equivalent of sevochlorane.

The alkali or alkaline earth metal iodides, or the linear or branched chain tetra-alkyl quarternary ammonium iodides, which may act as the catalytic agent in the halogen exchange reaction in the second step of the process of the present invention, include, but are not limited to NaI, KI, CsI, $KI_3$, $CaI_2$, $MgI_2$, $SrI_2$ or tetrabutyl ammonium iodide. Preferably, the iodide of potassium is employed in the reaction. The reaction employs between 0.01 and 0.5 equivalents of potassium iodide for each equivalent of sevochlorane. Preferably, the reaction employs between 0.05 and 0.15 equivalents of potassium iodide for each equivalent of sevochlorane.

The addition of sub-stoichiometric quantities of potassium iodide significantly increases the velocity of the conversion of sevochlorane to sevoflurane in different solvents.

It is well known that halogen exchange reactions depend on the solvent. Sulfolane was the solvent used for the halogen exchange reaction in the first preparations described for sevoflurane, in German patent 1954268 and U.S. Pat. No. 3,689,571. Although the U.S. Pat. No. 6,100,434 mentions various solvents considered adequate for the conversion of sevochlorane to sevoflurane using potassium fluoride (KF), the solvents that were in fact tested, were diethylene glycol and polyethyleneglycol 400 (PEG 400). The inventors also mentioned the conversion of sevochlorane to sevoflurane in a non-polar solvent in combination with a phase transfer catalyst such as a ($C_8$-$C_{10}$) methyl trialkylammonium chloride, however, no examples are presented.

According to the present invention, the utilization of KI together with KF increased significantly the velocity of the conversion of sevochlorane to sevoflurane not only in PEG 400 and sulfolane, but principally in solvents, where without the addition of KI, the reaction would be inviable. In addition, the utilization of KI together with KF allows reduction of the solvent quantity and the increase of the reactants concentration in the reaction medium results in higher yield and purity of the isolated product. It also allows the reaction be conducted with a lower quantity of KF.

Preferably, the second step of the reaction is conducted in the presence of a solvent. During the development of the process, various solvents were employed, among them: sulfolane, polar solvents such as dimethylformamide (DMF), dimethyl sulfoxide (DMSO), dimethylacetamide (DMAC), N-methyl pyrolidone, 1,3-dimethyl-imidazolidin-2-one (DMI), propylene glycol (PG), a mixture of medium chain length mono- and diglycerides (MDGCM), a mixture of mono-, di- and triglycerides and mono- and diesters of polyethylene glycol (LB), 1-methoxy-2-propanol (MP), polypropylene glycol (PPG), polyethylene glycol (PEG), esters and ketones.

Mixtures of medium chain length mono- and diglycerides are known and commercially available. For example, a mixture of mono- and diglycerides of medium chain length of $C_8$-$C_{10}$, is commercially available under the trade name Alkoline™.

Mixtures of mono-, di- and triglycerides and mono- and diesters of polyethylene glycol are known and commercially available under the trade name Labrafil. For example, Labrafil M 2125 CS™ may be obtained by partial alcoholysis of unsaturated oil containing principally triglycerides of linoleic acid using polyethylene glycol with a relative, median molecular weight between 300 e 400.

The conversion of sevochlorane to sevoflurane is monitored by gas chromatography by analysis of the gaseous phase of the reaction medium until complete consumption of the sevochlorane or by removal of the sevoflurane formed in the reaction medium by fractional distillation, shifting the equilibrium to favor formation of the product. The peaks corresponding to sevoflurane and sevochlorane are integrated in the chromatograms. The conversion is the percentage of sevoflurane observed in the chromatogram.

Sevoflurane is isolated by fractional distillation or by the addition of water and separation of the phases, and then by distillation of the organic phase. The sevoflurane obtained is washed with an alkaline solution to remove fluoride ions, and subsequently washed with a solution of sodium bisulfite to remove iodine and finally, washed with water. The percentage yield is calculated by the following equation:

% Yield=(mols of obtained sevoflurane/mols of initially employed sevochlorane)×100

Considering the steps involving treatment of the intermediate sevochlorane and the isolation of the product sevoflurane, the process for the preparation of fluoromethyl 2,2,2-trifluoro-1-(trifluoromethyl)ethyl ether (sevoflurane) of the present invention is characterized by inclusion of the following steps:

reacting hexafluoroisopropanol with paraformaldehyde, sulfuric acid and thionyl chloride, maintaining the reaction mixture under stirring to form the intermediate sevochlorane;

treating the crude sevochlorane with an aqueous solution of sodium carbonate to neutralize it;

treating the neutral sevochlorane with an aqueous solution of sodium hydroxide to remove by-products;

converting sevochlorane to sevoflurane with potassium fluoride (KF) in the presence of a sub-stoichiometric quantity of potassium iodide (KI) and a solvent;

isolating the sevoflurane by the addition of water, separation of the organic phase and distillation, or by direct distillation of the reaction mixture; and purificating the sevoflurane by fractional distillation.

The following examples are presented for illustrative purposes only, and are not intended to limit the scope of the present invention.

EXAMPLE 1

Preparation of Sevochlorane. Effect of the Quantity of the Reagents on the Yield and Purity of the Product Table 1 presents the results of a series of experiments, which were accomplished with the purpose of investigating the influence of the quantity of the reagents on the yield and purity of the product sevochlorane. In each of the experiments 1 equivalent of HFIP was used and the number of equivalents of the remaining reagents were varied as shown in Table 1.

TABLE 1

Influence of the quantity of the reagents on the yield and purity of the product sevochlorane.

| Trial | $SOCl_2$ (eq.) | $H_2SO_4$ (eq.) | $CH_2O$* (eq.) | Sevochlorane (%) | Yield (%) |
|---|---|---|---|---|---|
| 1 | 1.2 | 1 | 1 | 65.6 | 71.8 |
| 2 | 1.7 | 1 | 1 | 98.2 | 50.0 |
| 3 | 2.2 | 1 | 1 | 99.2 | 46.4 |
| 4 | 1.2 | 1.4 | 1 | 69.8 | 72.4 |
| 5 | 1.7 | 1.4 | 1 | 98.1 | 55.1 |
| 6 | 2.2 | 1.4 | 1 | 92.7 | 26.0 |
| 7 | 1.2 | 1.8 | 1 | 78.2 | 71.2 |
| 8 | 1.7 | 1.8 | 1 | 98.1 | 54.4 |
| 9 | 2.2 | 1.8 | 1 | 90.7 | 44.0 |
| 10 | 1.2 | 1 | 1.5 | 40.5 | 71.1 |
| 11 | 1.7 | 1 | 1.5 | 90.5 | 73.9 |
| 12 | 2.2 | 1 | 1.5 | 94.8 | 61.8 |
| 13 | 1.2 | 1.4 | 1.5 | 53.7 | 69.6 |
| 14 | 1.7 | 1.4 | 1.5 | 92.5 | 76.1 |
| 15 | 2.2 | 1.4 | 1.5 | 97.6 | 55.2 |
| 16 | 1.2 | 1.8 | 1.5 | 55.2 | 75.2 |
| 17 | 1.7 | 1.8 | 1.5 | 89.4 | 76.0 |
| 18 | 2.2 | 1.8 | 1.5 | 97.4 | 45.9 |
| 19 | 1.2 | 1 | 2 | 24.4 | 75.4 |
| 20 | 1.7 | 1 | 2 | 72.1 | 73.3 |
| 21 | 2.2 | 1 | 2 | 93.2 | 66.9 |
| 22 | 1.2 | 1.4 | 2 | 23.6 | 81.0 |
| 23 | 1.7 | 1.4 | 2 | 66.4 | 84.4 |
| 24 | 2.2 | 1.4 | 2 | 92.2 | 72.4 |
| 25 | 1.2 | 1.8 | 2 | 39.7 | 75.9 |
| 26 | 1.7 | 1.8 | 2 | 73.9 | 77.0 |
| 27 | 2.2 | 1.8 | 2 | 95.0 | 75.5 |

*The formaldehyde equivalent used was paraformaldehyde.

The general procedure involves a reactor equipped with mechanical or magnetic stirring, thermometer, an addition funnel and a refrigerated condenser, to which were added HFIP, paraformaldehyde and thionyl chloride. The condenser was connected through an U-shape glass tube to a vessel containing a 30% sodium hydroxide solution in order to neutralize the gasses generated in the reaction. Sulfuric acid was added slowly, via an addition funnel, maintaining the reaction temperature below 20° C. with an ice/water bath. The mixture was maintained under stirring for 6 hours. The stirring was stopped, the mixture was transferred to a separation funnel and the organic phase (upper phase) was returned to the reaction flask. The mixture was cooled to approximately 0° C. and a 10% sodium carbonate solution was added via an addition funnel until the aqueous phase attained a stable pH of 7, maintaining the temperature between 0° C. and 10° C. When the separation of phases in the reaction medium was not observed, the mixture was cooled to 0° C. and water was added until a clean separation of the phases occurred. In this case, the organic phase was then returned to reaction flask, the mixture was cooled to approximately 0° C. and a 10% sodium carbonate solution was added via an addition funnel until the aqueous phase attained a stable pH of 7, maintaining the temperature between 0° C. and 10° C. The sevochlorane isolated was analyzed by gas chromatography.

By means of treating the analytical data with statistic tools it can be realized the following statements. To obtain a sevochlorane with high purity it is employed 1.6 to 2.2 equivalents of thionyl chloride, 1.0 to 2.0 equivalents of sulfuric acid and 1.0 to 2.0 equivalent of formaldehyde per equivalent of HFIP (trials 2, 3, 5, 6, 8, 9, 11, 12, 14, 15, 18, 21, 24, 27). To obtain a sevochlorane with high purity and yield it is employed 1.7 to 2.0 equivalents of thionyl chloride, 1.0 to 2.0 equivalents of sulfuric acid and 1.5 to 2.0 equivalent of formaldehyde per equivalent of HFIP (trials 11, 14, 24 e 27). Preferably, it is employed 1.8 equivalents of thionyl chloride, 1.5 equivalent of sulfuric acid and 1.5 equivalent of formaldehyde per equivalent of HFIP.

EXAMPLE 2

Preparation of Sevochlorane. Effect of the Order of Addition of the Reagents

Table 2 presents the results of the experiments, which were accomplished with the purpose of investigating the influence of the order of addition of the reagents on the yield and purity of the product, sevochlorane. In each of the experiments 1 equivalent of HFIP, 1.8 equivalents of thionyl chloride, 1.5 equivalents of sulfuric acid and 1.5 equivalents of formaldehyde were used.

Reaction 1 corresponds to the addition of sulfuric acid to a mixture of HFIP, paraformaldehyde and thionyl chloride, while reaction 2 corresponds to the addition of thionyl chloride to a mixture of HFIP, paraformaldehyde and sulfuric acid.

TABLE 2

Influence of the order of addition of the reagents on the process for the preparation of sevochlorane according to the present invention.

| Reaction* | Yield (%) | Temp.** | Sevochlorane (%) | P1 (%) | HFIP (%) | Other by-products (%)*** |
|---|---|---|---|---|---|---|
| 1 | 76 | 20° C. | 99 | 0.3 | 0.2 | 0.5 |
| 2 | 71 | 35° C. | 98 | 0.2 | 0.1 | 1.7 |

*6 hours of reaction.
**temperature of the mixture HFIP, paraformaldehyde and (thionyl chloride or sulfuric acid).
***By-products: bisCl, P2 and P3

The general procedure involves a reactor equipped with mechanical or magnetic stirring, thermometer, addition funnel and a cooled condenser, to which were added the HFIP, paraformaldehyde and thionyl chloride or sulfuric acid. The condenser was connected through an U-shape glass tube to a vessel containing a 30% sodium hydroxide solution to neutralize the gasses generated in the reaction. Sulfuric acid or thionyl chloride was then added slowly, via an addition funnel under stirring, maintaining the reaction temperature below 20° C. with a water/ice bath. The resulting mixture was maintained under stirring and at a temperature between 15° C. and 35° C. for 6 hours. The mixture was then transferred to a separation funnel, and the phases were separated. The organic phase was treated with a 10% sodium carbonate solution until the pH turned basic, maintaining the temperature between 0° C. and 10° C. A 10% sodium hydroxide solution was added to this mixture which was then maintained under stirring for one hour. The product was isolated as a colorless liquid.

The results presented in Table 2 show that the order of addition of the reagents does not have a significant influence on the yield or purity of the sevochlorane obtained.

Reaction 2 showed a slight exothermic process during mixture of the HFIP and paraformaldehyde with sulfuric acid, raising the temperature of the reaction medium to 35° C. Although this behavior did not influence on the yield or purity of the product sevochlorane, the execution of the process for the preparation of sevochlorane according to the present invention preferably employs the order of addition of the reagents according to reaction 1.

EXAMPLE 3

Preparation of Sevochlorane from HFIP Under Optimized Conditions and Treatment of the Crude Sevochlorane In a reactor equipped with magnetic stirring, thermometer, addition funnel and a cooled condenser, there was added HFIP (317 mL; 3.0 mol; 1 eq.), paraformaldehyde (134 g, 4.47 mol; 1.5 eq.) and thionyl chloride (400 mL, 5.48 mol; 1.8 eq.). The condenser was connected through an U-shape glass tube to a vessel containing a 30% sodium hydroxide solution to neutralize the gasses generated in the reaction. Sulfuric acid (243 mL, 4.57 mol, 1.5 eq.) was added slowly, via an addition funnel and under stirring, maintaining the reaction temperature below 20° C. with a water/ice bath. The resulting mixture was maintained under stirring and at a temperature between 15° C. and 35° C. for 6 hours. An aliquot of the reaction mixture was cooled and treated with water and a 10% sodium carbonate solution, and then analyzed by gas chromatography showing the following composition: 97% sevochlorane, 0.3% P1, 0.01% HFIP and 2.4% bis-chloromethyl ether, P3 and P2. The stirring was stopped, and the mixture was transferred to a separation funnel and the organic phase (upper phase) was returned to the reaction flask. The mixture was cooled to approximately 0° C. and a 10% sodium carbonate solution (620 mL) was added via an addition funnel until the aqueous phase attained a stable pH of 7, maintaining the temperature between 0° C. and 10° C. A 10% sodium hydroxide solution (544 mL) was then added. The mixture was maintained under stirring for one hour and an aliquot of the organic phase was analyzed by gas chromatography which revealed the presence of 99% sevochlorane, 0.3% P1, 0.001% HFIP, 0.40% P3 and less than 0.5% of bis-chloromethyl ether. The mixture was transferred to a separation funnel. The product (lower phase) was separated, resulting in a colorless liquid (520 g; yield: 80%). Analysis by gas chromatography of the final product showed the following composition: sevochlorane (99.3%), HFIP (0.04%), P1 (0.3%), P2 and P3 (total of 0.4%).

EXAMPLE 4

Conversion of Sevochlorane to Sevoflurane Influence of the Presence of Potassium Iodide on the Velocity of the Reaction Table 3 presents the results of a series of experiments, which were accomplished with the purpose of investigating the influence of the presence of potassium iodide on the velocity of the conversion of sevochlorane to sevoflurane in different solvents. The solvents tested were: DMI (1,3-dimethyl-imidazolidin-2-one), DMF (dimethylformamide), PG (propylene glycol), LB (a mixture of mono-, di- and triglycerides and mono- and diesters of polyethylene glycol); MDGCM (a mono- and diglyceride of medium chain length), MP (1-methoxy-2-propanol), PPG 400 (polypropylene glycol having an average molecular weight of 400) and PEG 400 (polyethylene glycol having an average molecular weight of 400).

The general procedure involves a reactor equipped with magnetic stirring, thermometer and a refrigerated condenser, to which sevochlorane, the solvent, potassium fluoride (KF) and potassium iodide (KI) were added. The concentration of sevochlorane in the reaction medium was approximately 3.0 mol·L$^{-1}$. The mixture was maintained at reflux under stirring for a period of time inferior to 46 hours. At intervals of one hour, an aliquot of the gas phase of the reaction mixture was analyzed by gas chromatography.

TABLE 3

Influence of the presence of KI on the conversion of sevochlorane to sevoflurane.

| Reaction | Solvent | KF (eq.) | KI (eq.) | Conversion (%) | Time (h) |
|---|---|---|---|---|---|
| 1 | Sulfolane | 2.5 | — | 41 | 6 |
| 2 | Sulfolane | 2.5 | 0.15 | 88 | 4 |
| 3 | DMI | 2.5 | — | 89 | 9 |
| 4 | DMI | 2.0 | 0.15 | 95 | 5 |
| 5 | DMF | 2.5 | — | 36 | 10 |
| 6 | DMF | 1.5 | 0.15 | 95 | 3 |
| 7 | PG | 2.5 | — | 94 | 24 |
| 8 | PG | 1.5 | 0.15 | 99 | 3 |
| 9 | LB | 2.5 | — | 24 | 20 |
| 10 | LB | 1.5 | 0.15 | 95 | 6 |
| 11 | MDGCM | 2.5 | — | 96 | 24 |
| 12 | MDGCM | 1.5 | 0.15 | 95 | 4 |
| 13 | MP | 2.5 | — | 60 | 46 |
| 14 | MP | 1.5 | 0.05 | 92 | 4 |
| 15 | PPG 400 | 2.5 | — | 93 | 46 |
| 16 | PPG 400 | 1.5 | 0.15 | 95 | 4 |
| 17 | PEG 400 | 2.5 | — | 97 | 3 |
| 18 | PEG 400 | 1.5 | 0.15 | 99 | 2 |

The results presented in Table 3 demonstrate a significant increase in the velocity of the conversion of sevochlorane to sevoflurane caused by the addition of sub-stoichiometric quantities of potassium iodide. In addition, in the presence of a sub-stoichiometric quantity of KI, it is possible to considerably reduce the quantity of KF necessary for the conversion of sevochlorane to sevoflurane. Nonetheless, it is convenient to maintain a slight excess of KF in relation to sevochlorane to shift the equilibrium of the reaction to formation of sevoflurane.

EXAMPLE 5

Optimization of the Quantity of KF and KI for the Conversion of Sevochlorane to Sevoflurane Using a Mixture of Mono- and Diglycerides of Medium Chain Length as Solvent Table 4 presents the results of experiments, which were accomplished with the purpose of investigating the influence of the quantity of potassium fluoride and potassium iodide in the conversion of sevochlorane to sevoflurane. In total, there were performed 9 reactions varying the quantity of potassium fluoride in the range of 1.5 to 2.5 equivalents and the quantity of potassium iodide in the range of 0.05 to 0.15 equivalents per 1 equivalent of sevochlorane.

TABLE 4

Influence of the number of equivalents of KF and KI on the conversion using a mixture of mono- and diglycerides of medium chain length as solvent.

| | | | Conversion % | | | | | |
|---|---|---|---|---|---|---|---|---|
| Reaction | KF (eq) | KI (eq) | 1 h | 2 h | 3 h | 4 h | 5 h | 6 h |
| 1 | 1.5 | 0.05 | 63.1 | 81.8 | 82.4 | 92.7 | 95.3 | 97.0 |
| 2 | 2.0 | 0.05 | 60.4 | 78.6 | 83.9 | 92.5 | 97.9 | 98.8 |
| 3 | 2.5 | 0.05 | 67.9 | 84.8 | 95.3 | 98.3 | 99.7 | 98.9 |
| 4 | 1.5 | 0.10 | 72.2 | 88.3 | 94.4 | 97.0 | 98.6 | 99.5 |
| 5 | 2.0 | 0.10 | 76.9 | 89.9 | 94.5 | 96.8 | 98.1 | 98.2 |
| 6 | 2.5 | 0.10 | 70.8 | 86.6 | 92.2 | 95.3 | 97.1 | 97.2 |
| 7 | 1.5 | 0.15 | 77.8 | 89.4 | 94.1 | 96.8 | 98.4 | 99.2 |
| 8 | 2.0 | 0.15 | 79.1 | 90.6 | 92.9 | 97.0 | 98.3 | 99.0 |
| 9 | 2.5 | 0.15 | 79.6 | 89.5 | 93.7 | 95.9 | 97.6 | 98.4 |

The general procedure involves a reactor equipped with magnetic stirring, thermometer and a refrigerated condenser, to which sevochlorane, the solvent, potassium fluoride and potassium iodide were added. The concentration of sevochlorane in the reaction medium was around 3.0 mol·L$^{-1}$. The mixture was maintained at reflux under stirring for 6 hours. At intervals of one hour, an aliquot of the gas phase of the reaction mixture was analyzed by gas chromatography.

The results presented in Table 4 show that conversions above 94% was observed after three hours of reaction for the conditions in reactions 3, 4, 5 and 7, and conversions above 99% after six hours for the conditions in reactions 7 and 8. The conditions used in reaction 7 were chosen for the determination of the yield in this step and of the effects on the treatment and isolation of the product.

EXAMPLE 6

Conversion of Sevochlorane to Sevoflurane According to the Conditions Employed in Reaction 7 of Example 5

In a reactor equipped with magnetic stirring, thermometer and a refrigerated condenser, sevochlorane (100 g, 0.5 mol, 1 eq.), a mixture of mono- and diglycerides of medium chain length (155 mL), potassium fluoride (40.3 g, 0.7 mol, 1.50 eq.) and potassium iodide (11.50 g, 0.07 mol, 0.15 eq were added). The mixture was maintained under stirring at reflux for three hours and then submitted to fractional distillation to provide sevoflurane (60 g; 0.3 mol; 60%).

EXAMPLE 7

Conversion of Sevochlorane to Sevoflurane According to the Conditions of the Reaction 7 of Example 5 Scale-Up and Separation of Sevoflurane from the Reaction Medium by Distillation after 1.5 Hours of Reaction In a reactor equipped with magnetic stirring, thermometer, a Vigreaux column packed with pieces of polypropylene (in order to increase the efficiency of the column) and a refrigerated condenser, sevochlorane (350 g, 1.62 mol, 1 eq.), the mono-e diglycerides of medium chain length (541 mL, 2.99 M), potassium fluoride (141 g, 2.4 mol, 1.50 eq.) and potassium iodide (40.2 g, 0.2 mol, 0.15 eq.) were added. The mixture was maintained under stirring at reflux for 1.5 hours and then submitted to fractional distillation maintaining the temperature of the distillate at 50° C. to provide sevoflurane with above 99% purity (246 g; 1.23 mol; 76%).

EXAMPLE 8

Conversion of Sevochlorane to Sevoflurane Using Polyethylene Glycol 400 as Solvent. Distillation of the Reaction Medium after 1.5 Hours of Reaction In a reactor equipped with magnetic stirring, thermometer, a Vigreaux column packed with pieces of polypropylene (in order to increase the efficiency of the column) and a refrigerated condenser, sevochlorane (350 g, 1.62 mol, 1 eq.), polyethylene glycol 400 (541 mL), potassium fluoride (141 g, 2.4 mol, 1.50 eq.) and potassium iodide (40.3 g, 0.2 mol, 0.15 eq.) were added. The mixture was maintained under stirring at reflux for 1.5 hours and then submitted to fractional distillation maintaining the temperature of the distillate at 50° C. to provide sevoflurane with above 99% purity (256 g; 1.28 mol; 79%).

EXAMPLE 9

Conversion of Sevochlorane to Sevoflurane Using Propylene Glycol as a Solvent. Distillation of the Reaction Medium after 1.5 Hours of Reaction. Effect of the Concentration of the Reaction Medium on the Yield of the Reaction Table 5 presents the results of experiments, which were accomplished with the purpose of investigating the influence of the concentration of sevochlorane in the reaction medium on the conversion of sevochlorane to sevoflurane using propylene glycol as solvent. The increased concentration of sevochlorane in the reaction medium resulted in higher yield.

The general procedure involves a reactor equipped with magnetic stirring, thermometer, and a refrigerated condenser, to which sevochlorane (350 g, 1.62 mol, 1 eq.), propylene glycol (541 mL or 270 mL), potassium fluoride (141 g, 2.4 mol, 1.50 eq.) and potassium iodide (40.3 g, 0.2 mol, 0.15 eq.) were added. The mixture was maintained under stirring at reflux for 1.5 hours and then submitted to fractional distillation maintaining the temperature of the distillate at 50° C. to provide sevoflurane with above 99% purity.

TABLE 5

Influence of the concentration of sevochlorane in the reaction medium on the yield of the reaction using propylene glycol as solvent.

| Reaction | Concentration of sevochlorane (mol · L⁻¹) | KF (eq) | KI (eq) | Time (h) | Yield (%) |
|---|---|---|---|---|---|
| 1 | 3.0 | 1.5 | 0.15 | 2 | 52 |
| 2 | 6.0 | 1.5 | 0.15 | 2 | 63 |

EXAMPLE 10

Conversion of Sevochlorane to Sevoflurane Using Polyethylene Glycol 400 as Solvent. Isolation of the Product by Addition of Water, Separation of the Organic Phase and Purification by Fractional Distillation In a reactor equipped with magnetic stirring, thermometer and a refrigerated condenser, sevochlorane (350 g, 1.62 mol, 1 eq.), polyethylene glycol 400 (541 mL), potassium fluoride (141 g, 2.4 mol, 1.50 eq.) and potassium iodide (40.3 g, 0.2 mol, 0.15 eq.) were added. The mixture was maintained under stirring at reflux for 2 hours and then water (540 mL) was added, the phases were separated and the organic phase washed with a 2% sodium carbonate solution (2×155 mL), a 2% sodium bisulfite solution (155 mL) and water (155 mL). The crude product was submitted to fractional distillation to provide sevoflurane with above 99.9% purity (214 g; 1.07 mol; 66%).

EXAMPLE 11

Conversion of Sevochlorane to Sevoflurane Using Polyethylene Glycol 400 as Solvent. Effect on the Quantity of PEG 400 Employed on the Yield when the Product is Isolated by the Addition of Water, Separation of the Organic Phase and Purification by Fractional Distillation Table 6 presents the results of experiments, which were accomplished with the purpose of investigating the influence of the quantity of polyethylene glycol on the yield of the reaction for conversion of sevochlorane to sevoflurane, which was isolated by the addition of water to the reaction medium, separation of the organic phase and purification by fractional distillation.

TABLE 6

Effect of the quantity of polyethylene glycol 400 on the yield of the reaction.

| Reaction | Concentration of sevochlorane (mol · L⁻¹) | KF (eq.) | KI (eq.) | Conversion (%) | Time (h) | Yield (%) |
|---|---|---|---|---|---|---|
| 1 | 3 | 1.5 | 0.15 | 99 | 2 | 66 |
| 2 | 6 | 1.5 | 0.15 | 99 | 2 | 76 |
| 3 | 7.5 | 1.5 | 0.15 | 99 | 2 | 74 |
| 4 | 15 | 1.5 | 0.15 | 97 | 2 | 73 |

The general procedure involves a reactor equipped with magnetic stirring, thermometer and a refrigerated condenser, to which sevochlorane, polyethylene glycol 400, potassium fluoride (KF) and potassium iodide were added. The mixture was maintained at reflux under stirring until the complete conversion of sevochlorane to sevoflurane. The product was isolated by the addition of water and the organic phase was washed with a 2% sodium carbonate solution, a 1% sodium bisulfite solution and water. The product was purified by fractional distillation to provide sevoflurane with above 99% purity.

Based on the results presented in Table 6, it can be realized that the decrease of the quantity of PEG 400 employed in the reaction results in a yield increase, in addition to process cost reduction in function of the lower quantities of solvent required for the reaction and of residues generated.

The invention claimed is:

1. A process for the preparation of fluoromethyl 2,2,2-trifluoro-1-(trifluoromethyl)ethyl ether (sevoflurane) comprising the following steps:
    (i) reacting hexafluoroisopropanol (HFIP) with: a formaldehyde equivalent selected from the group consisting of paraformaldehyde and 1,3,5-trioxane; a chlorinating agent selected from the group consisting of oxalyl chloride, sulfuryl chloride and thionyl chloride; and a concentrated or fuming sulfuric acid, wherein the reactants are combined in a way selected from the group consisting of a) adding the sulfuric acid to a mixture of HFIP, formaldehyde equivalent and chlorinating agent; and b) adding the chlorinating agent to a mixture of HFIP, formaldehyde equivalent and sulfuric acid; and c) adding the HFIP to a mixture of the formaldehyde equivalent, sulfuric acid and chlorinating agent, thereby generating chlorosulfonic acid and chloromethylating the HFIP in the same pot to form sevochlorane; and
    (ii) reacting sevochlorane with an alkali metal fluoride, or with a linear or branched chain tetra-alkyl, quaternary ammonium fluoride in the presence of a sub-stoichiometric quantity of an alkali metal iodide, or of a linear or branched chain tetra-alkyl, quaternary ammonium iodide, to form sevoflurane.

2. The process according to claim 1, characterized by the fact that the formaldehyde equivalent is paraformaldehyde and the chlorinating agent is thionyl chloride.

3. The process according to claim 2, characterized by the fact that the reaction in the first step employs 1.6 to 2.0 molar equivalents of thionyl chloride, 1.0 to 2.0 molar equivalents of sulfuric acid and 1.0 to 2.0 molar equivalents of paraformaldehyde per molar equivalent of hexafluoroisopropanol.

4. The process according to claim 3, characterized by the fact that the reaction in the first step employs 1.8 molar equivalents of thionyl chloride, 1.5 molar equivalents of sulfuric acid and 1.5 molar equivalents of paraformaldehyde per molar equivalent of hexafluoroisopropanol.

5. The process according to claim 1, characterized by the fact that the reaction in the first step is conducted at a temperature between 0° C. and 60° C.

6. The process according to claim 1, characterized by the fact that the alkali metal fluoride is potassium fluoride (KF).

7. The process according to claim 1, characterized by the fact that the alkali metal iodide is potassium iodide (KI).

8. The process according to claim 1 characterized by the fact that the reaction in the second step employs between 1.5 and 2.5 molar equivalents of KF and between 0.05 and 0.15 molar equivalents of KI per molar equivalent of sevochlorane.

9. The process according to claim 1, characterized by the fact that the reaction in the second step is conducted at a temperature between 60° C. and 100° C. and at a pressure between 0 psi to 30 psi.

10. The process according to claim 1, characterized by the fact that the reaction (ii) is conducted in the presence of a solvent selected from the group consisting of sulfolane, dimethylformamide (DMF), dimethyl sulfoxide (DMSO), dimethylacetamide (DMAC), N-methyl pyrrolidone, 1,3-dimethyl-imidazolidin-2-one (DMI), propylene glycol, a mixture of mono- and diglycerides of medium chain length, a mixture of mono-, di- and triglycerides and mono- and diesters of polyethylene glycol, 1-methoxy-2-propanol, polypropyleneglycol, polyethylene glycol and combinations thereof.

11. The process according to claim 10, characterized by the fact that the solvent is employed in a quantity that results in a concentration of sevochlorane in the reaction medium in the range of 3 to 15 mol·L$^{-1}$.

12. The process according to claim 1, comprising an additional step of treating the sevochlorane with a first aqueous alkaline solution of an alkali or alkaline earth metal carbonate or hydroxide, or with ammonia to neutralize the sevochlorane.

13. The process according to claim 12, characterized by the fact that the first aqueous alkaline solution is a sodium carbonate solution.

14. The process according to claim 1, comprising an additional step of treating the neutral sevochlorane with a second aqueous alkaline solution of an alkali or alkaline earth metal hydroxide to remove reaction by-products.

15. The process according to claim 14, characterized by the fact that the second aqueous alkaline solution is a sodium hydroxide solution.

16. The process according to claim 1, comprising an additional step in which the sevoflurane is distilled.

17. A process for the preparation of fluoromethyl 2,2,2-trifluoro-1-(trifluoromethyl)ethyl ether (sevoflurane) which consists of the following steps:
  (i) reacting hexafluoroisopropanol with paraformaldehyde, sulfuric acid and thionyl chloride to form the intermediate sevochlorane, wherein said step is carried out by:
  a) adding the hexafluoroisopropanol (HFIP), 1.5 molar equivalents of paraformaldehyde and 1.8 molar equivalents of thionyl chloride per molar equivalent of HFIP to a reaction vessel;
  b) adding 1.5 molar equivalents of sulfuric acid per molar equivalent of HFIP, under stirring, to the reaction mixture of item a), maintaining the reaction temperature below 20° C. until this step is completed;
  c) maintaining the reaction mixture under stirring at a temperature ranging between 0° C. and 60° C.;
  d) separating a resulting organic phase comprising sevochlorane;
  (ii) treating the organic phase comprising sevochlorane with an aqueous solution of sodium carbonate to neutralization;
  (iii) treating the neutral organic phase comprising sevochlorane with an aqueous solution of sodium hydroxide to decompose and remove by-products;
  (iv) converting the sevochlorane to sevoflurane by reacting the sevochlorane with potassium fluoride (KF) in the presence of 0.15 molar equivalents of potassium iodide per molar equivalent of sevochlorane, and a solvent;
  (v) isolating the sevoflurane by addition of water, separation of the organic phase and distillation, or by direct distillation of the reaction mixture; and
  (vi) purifying the sevoflurane by fractional distillation.

18. A process according to claim 17, characterized by the fact that the solvent in the step (iv) is selected from the group consisting of sulfolane, 1,3-dimethyl-imidazolidin-2-one (DMI), dimethylformamide (DMF), dimethyl sulfoxide (DMSO), dimethylacetamide (DMAC), N-methyl pyrrolidone, propylene glycol, a mixture of mono- and diglycerides of medium chain length, a mixture of mono-, di- and triglycerides and mono- and diesters of polyethylene glycol, 1-methoxy-2-propanol, polypropyleneglycol, polyethylene glycol or combinations thereof.

* * * * *